United States Patent [19]

Crossland et al.

[11] Patent Number: 5,409,823
[45] Date of Patent: Apr. 25, 1995

[54] METHODS FOR THE PRODUCTION OF HYBRID SEED

[75] Inventors: Lyle D. Crossland, Chapel Hill; Annmarie Tuttle, Garner; Jeffrey I. Stein, Chapel Hill, all of N.C.

[73] Assignee: Ciba-Geigy Corporation, Ardsley, N.Y.

[21] Appl. No.: 950,348

[22] Filed: Sep. 24, 1992

[51] Int. Cl.$^6$ .................. C12N 15/82; C12N 15/79; A01H 5/00

[52] U.S. Cl. .................. 435/172.3; 435/172.1; 800/205; 935/35; 935/36; 935/64; 47/DIG. 1; 536/24.1

[58] Field of Search .................. 435/172.3, 172.1; 800/205; 935/35, 36, 64; 47/DIG. 1; 536/24.1

[56] References Cited

U.S. PATENT DOCUMENTS

| | | | |
|---|---|---|---|
| 4,833,080 | 5/1989 | Brent et al. | 435/172.3 |
| 4,952,496 | 8/1992 | Studier et al. | 435/91 |
| 4,990,607 | 5/1991 | Katagiri et al. | 536/23.6 |
| 5,122,457 | 6/1992 | Reim et al. | 435/69.1 |
| 5,126,251 | 6/1992 | Moss et al. | 435/69.1 |
| 5,135,855 | 8/1992 | Moss et al. | 435/69.1 |

FOREIGN PATENT DOCUMENTS

| | | |
|---|---|---|
| 0321201 | 6/1989 | European Pat. Off. |
| WO88/10430 | 6/1988 | WIPO |
| WO89/10396 | 11/1989 | WIPO |
| WO90/08828 | 8/1990 | WIPO |
| WO90/08830 | 8/1990 | WIPO |
| WO92/01799 | 2/1992 | WIPO |

OTHER PUBLICATIONS

Katagiri et al 1992 (Jan.) Trends in Genetics 8:22–26.
Vetten et al., *ISPMB Program and Abstract*, 265 (1991) [held Tucson Ariz. 3rd International Congress 6–11 Oct. 1991].
Benton et al., *Molecular and Cellular Biology*, 10:353–360 (1990).
Brent et al., *Cell*, 43:729–736 (1985).
Carey et al., *J. Mol. Biol.*, 209:423–432 (1989).
Cech et al., *Ann. Rev. Biochem.*, 55:599–629 (1986).
Cech, *Science*, 236:1532–1539 (1987).
Cech, *Gene*, 73:259–271 (1988).
Deng et al; *Gene*, 109:193–201 (1991).
Cress et al, *Science*, 251:87–90 (1991).
Dubendorff et al., *J. Mol. Bio.*, 219:45–59 (1991).
Dubendorff et al., *J. Mol. Biol.*, 219:61–67 (1991).
Dunn et al., *Gene*, 68:259–266 (1988).
Fedor et al., *Proc. Natl. Acad. Sci, USA*, 87:1668–1672 (1990).
Fuerst et al., *Proc. Natl. Acad. Sci, USA*, 83:8122–8126 (1986).
Fuerst et al., *J. Mol. Biol.*, 206:333–348 (1989).
Fuerst et al., *Molecular and Cellular Biology*, 7:2538–2544 (1987).
Giniger et al., *Cell*, 40:767–774 (1985).
Haseloff et al., *Nature*, 334:585–591 (1988).

(List continued on next page.)

*Primary Examiner*—Patricia R. Moody
*Attorney, Agent, or Firm*—W. Murray Spruill

[57] ABSTRACT

The present invention provides a dual method for producing male-sterile plants. Two genetically transformed plants, parents 1 and 2 are crossed to obtain male-sterile offspring. Parent 1 is transformed with an expression cassette comprising a nucleotide sequence encoding an anther-specific promoter which is operably linked to a nucleotide sequence encoding a transactivator. Parent 2 is transformed with an expression cassette comprising a target nucleotide sequence, which is capable of being activated by the transactivator, operably linked to a nucleotide sequence which encodes RNA or a polypeptide which will disrupt the formation of viable pollen. Therefore, crossing parent 1 with parent 2 results in male-sterile offspring. The male-sterile plants are useful for producing hybrid seed.

The invention also provides compositions and methods for high level expression of a coding region of interest in a plant.

16 Claims, No Drawings

OTHER PUBLICATIONS

Lassner et al., *Plant Molecullar Biology*, 17:229–234 (1991).
Lieber et al., *Nucleic Acids Research*, 17:8485–8493 (1989).
Lommel et al., *Virology*, 181:382–385 (1991).
Moffatt et al., *Plant Physiol*, 86:1150–1154 (1988).
Moss et al., *Nature*, 348:91–92 (1990).
Moss et al., "Rapid, Versatile and Simple System for Expressing Genes in Eukaryotic Cells", pp. 1–20 (Jul. 1989) NTIS Report No. PB90-114752.
Rodriguez et al., *Journal of Virology*, 64:4851–4857 (1990).
Rosenberg et al., *Gene*, 56:125–135 (1987).
Sadowski et al., *Nature*, 335:563–564 (1988).
Elroy-Stein et al., *Proc. Natl. Acad. Sci., USA*, 86:6126–6130 (1989).
Elroy-Stein et al., *Proc. Natl. Acad. Sci. USA*, 87:6743–6747 (1990).
Vennema et al., *Gene*, 108:201–209 (1991).
Zaug et al., *Science*, 2:470–475 (1986).

METHODS FOR THE PRODUCTION OF HYBRID SEED

FIELD OF THE INVENTION

The invention relates to the production of male-sterile plants and the use of such plants in producing hybrid seed.

BACKGROUND OF THE INVENTION

Heterosis in corn has received considerable attention because of its marked effect on yield improvement. This increased productivity on crossing different strains of corn was first noted in the late 19th century and was then developed according to systematic genetic procedures.

The usual method for raising hybrid corn is to establish many inbred lines, make intercrosses, and determine which hybrids are more productive in a given locality.

The success of hybrid maize motivated plant breeders to explore the existence and magnitude of hybrid vigor in many other species with economic importance. In general, hybrids increase yields. They are usually more efficient in use of growth factors and give a greater return per unit for the growth factors such as water and fertilizer. Under stress $F_1$ hybrids are generally superior to parental cultivars, with a more stable performance over a wide range of environments. With hybrids, there is uniformity in product and maturity that often facilitates harvest and increases the value of the product in the marketplace. The $F_1$ hybrid may combine characters that are difficult or impossible to combine in other ways. This is particularly true of many interspecific and intergeneric hybrids. The general conclusion from research is that hybrid vigor, a common phenomenon in plants is of sufficient magnitude to warrant commercial exploitation if appropriate techniques can be devised.

Hybrid vigor has been recognized as a wide-spread phenomenon in plants and animals for many years. Commercial hybrids are now used extensively in many crops, including corn, sorghum, sugarbeet, and sunflower. Research is being conducted on many other crops that may permit the wide-spread use of commercial hybrids in the future.

Commercial hybrids have the greatest potential for crops in which the hybrid seed can be produced reliably and economically. Three biological requirements for successful hybrid seed production include the presence of hybrid vigor, elimination of fertile pollen in the female parent, and adequate pollination by the male parent.

In order to produce hybrid seed uncontaminated with selfed seed, pollination control methods must be implemented to ensure cross-pollination and not self-pollination. Known pollination control mechanisms are generally mechanical, chemical, or genetic.

Elimination of fertile pollen from the female parent can be achieved by hand emasculation in some species such as maize, a monoecious species. Such elimination of fertile pollen is achieved by pulling or cutting the male inflorescence (tassel) from plants in the female parent population. This simple procedure prevents self-fertilization by mechanically detasseling female plants before pollen shed to prevent selfing. However, most major crop plants of interest have both functional male and female organs within the same flower. Thus, emasculation is not a simple procedure. At any rate, this form of hybrid seed production is extremely labor intensive and hence expensive.

To eliminate the laborious detasseling that is necessary to prevent self-fertilization in hybrid crosses, cytoplasmic factors which produce male-sterility have been used in some species in conjunction with restorer genes.

Male-sterility in the female parent can be controlled by nuclear genes or by a cytoplasmic-genetic system. Genetic male-sterility is controlled by nuclear genes in which the alleles for sterility generally are recessive to the alleles for fertility. Genetic male-sterility occurs in many species. Usually, it is controlled by a single recessive gene that must be homozygous to cause male-sterility. Breeders who use genetic male-sterility for hybrid seed production usually develop a phenotypically uniform female line that segregates 1:1 for Msms and no Msms individuals. Seed for these lines is increased in isolation by harvesting seed from msms plants that are pollinated from Msms plants. To produce commercial $F_1$ hybrid seed with genetic male-sterility, the 50 percent of female Msms plants must be rouged from the field as soon as their fertility can be identified. The labor associated with rouging fertile plants from female plants has greatly restricted the use of genetic male-sterility in producing hybrid seed. There are several problems associated with this system for producing commercial hybrid seed. First, it is not possible to eliminate fertile plants from the desired male-sterile plants in the female population. Genetic male-sterile plants must be maintained by mating them with male-fertile individuals. Half of the $F_1$ plants from such a cross would be sterile, but the remaining plants would be fertile. Thus, the unwanted male-fertile plants in the female population may disseminate pollen and reduce the effectiveness of the desired male parent.

The successful use of cytoplasmic male-sterility for commercial hybrid seed production requires a stable male-sterile cytoplasm, an adequate pollen source, and an effective system of getting the pollen from the male parent to the male-sterile female. Also, the cytoplasmic-genetic system of male sterility requires three lines to produce a single crossed hybrid; the A line (male-sterile), B line (male-fertile maintainer), and R line (male-fertile with restorer genes). Three-way crosses produced with cytoplasmic-genetic male sterility involved maintenance and production of four lines, an A and B line of one inbred and male-fertile inbreds of the other two.

Furthermore, the southern corn blight caused by *Helminthosporium maydis*, Race T, which severely attacked all maize hybrids with cytoplasmic male-sterile T cytoplasm, demonstrated the vulnerability of a hybrid seed production industry based on a single source of male-sterile cytoplasm. For hybrid maize, most seed producers have returned to hand or mechanical emasculation and wind pollination.

Hybrid seed may also be produced by the use of chemicals that block or kill viable pollen formation. These chemicals, gametocides, are used to impart a transitory male-sterility. However, the expense and availability of the chemicals and the reliability of the applications limits the production of hybrid seed by using gametocides.

Molecular methods for hybrid seed production have also been described. Such methods transform plants with constructs containing anti-sense DNA and other genes which are capable of controlling the production of fertile pollen into plants. Such regenerated plants are functionally male-sterile and are used for the production of hybrid seed by crossing with pollen from male-fertile plants. The primary deficiencies of these approaches stem from the fact that the genetically engineered male sterility gene, whether it is an anti-sense or RNAse, can only be maintained in a heterozygous state. They are fundamentally the same as natural genetic male steriles in that they must be maintained by crossing to isogenic male fertile lines. This is most problematic in the hybrid cross field where the acreage is large and yield is critical. The heterozygous female parent, of which only 50% will be male sterile, must be planted in rows next to the pollen donor male parent and the 50% fertile female parents removed. This is rendered easier in genetically engineered genetic male steriles because a herbicide resistance gene can be linked to the male sterility gene, and herbicide spray can be used to remove the fertile plants, but it still means that the female parent rows must be planted at double density in order to get the same yield per acre of our system. This will cause some yield loss due to competition. The herbicide spray also means yield loss because the resistant plants are never 100% immune to the herbicide, and the costs of spraying the chemical are considerable.

Accordingly, there is a need for a reliable simple technique for the formation of hybrid seed production.

SUMMARY OF THE INVENTION

The present invention is drawn to a method for producing male-sterile plants. The method comprises crossing two genetically transformed plants, parents 1 and 2. Parent 1 is transformed with an expression cassette which comprises a nucleotide sequence which encodes a first polypeptide, a transactivator, capable of regulating a second nucleotide sequence, a target nucleotide sequence. The DNA sequence encoding the first polypeptide is operably linked to an anther specific promoter.

Parent 2 is transformed with an expression cassette which comprises the target nucleotide sequence operably linked to a nucleotide sequence which encodes RNA or a polypeptide, both of which are capable of disrupting the formation of viable pollen. When parents 1 and 2 are crossed, polypeptide 1, the transactivator, regulates the target nucleotide sequence and turns on the expression of polypeptide 2. Thus, no viable pollen is formed in the subsequent generation.

The male-sterile plants are useful for producing hybrid seed.

The invention is further drawn to compositions and methods for high level expression of a heterologous gene in plants. In this manner, a first construct comprises a 5' regulatory region of interest operably linked to a nucleotide sequence which encodes a T7 polymerase. A second construct comprises the coding region of a polypeptide of interest operably linked to a T7 5' regulatory region. When a plant has been transformed with both constructs, high level expression of the polypeptide of interest is regulated by the T7 polymerase. By utilizing specific plant promoters to direct expression of the T7 polymerase, high levels of a polypeptide or RNA of interest can be obtained in specific tissues or at specific developmental stages.

DETAILED DESCRIPTION OF THE INVENTION

A dual system for production of male-sterile plants is provided. The system involves crossing two genetically transformed plants, herein referred to as parents 1 and 2. Parent 1 is transformed with an expression cassette which comprises a nucleotide sequence which directs the expression of a first polypeptide in anthers. This first polypeptide is capable of regulating the transcription of a second nucleotide sequence, the target DNA, which directs expression of RNA or a second polypeptide capable of disrupting the production of viable pollen. Parent 2 is transformed with an expression cassette which comprises the target nucleotide sequence operably linked to a nucleotide sequence which encodes RNA or a polypeptide capable of disrupting the formation of viable pollen.

As noted, the RNA or the second polypeptide can only be expressed when in the presence of the first polypeptide, the transactivator. Thus, both parents 1 and 2 are male-fertile. However, upon crossing parent 1 with parent 2, the transactivator regulates the expression of the RNA or polypeptide 2 via the target DNA sequence. The result is no viable pollen is produced. The resulting progeny containing both expression cassettes are male sterile.

Male sterility is the failure or inability to produce functional or viable pollen. Male sterility may result from defects leading to the non-formation of pollen or to the lack of functional ability in the pollen when it is formed. Therefore, either pollen is not formed or, if formed, it is either non-viable or incapable of effective fertilization under normal conditions.

The male-sterile plants of the invention, are female fertile. That is, the plants do not produce fertile pollen, yet are capable of accepting pollen from the desired paternal parent resulting in fertilization and seed production.

There are several transactivator polypeptides which can be used in the present dual sterility system. The important aspect is that the RNA or the second polypeptide which disrupts pollen formation is not expressed in the absence of the first or transactivator polypeptide.

The transactivators of the invention are capable of activating a target nucleotide sequence which is operably linked to a nucleotide sequence which encodes RNA or a second polypeptide both of which are capable of disrupting the production of viable pollen. Thus, the nucleotide sequence operably linked to the target sequence is only expressed in the presence of the transactivator.

The transactivators of the invention include, but are not limited to, polymerases, DNA binding proteins, naturally occurring and synthetic transcriptional activators, translational activators, post-transcriptional activators, and the like. The use of such transactivator polypeptides in directing expression of another nucleotide sequence is exemplified by the T7 RNA polymerase. See, U.S. Pat. Nos. 5,122,457; 5,126,251; and 5,135,855; Lassner et al., (1991) *Plant Molecular Biology* 17:229–234; Rodriguez et al., (1990) *Journal of Virology* 64:4851–4857; Vennema et al., (1991) *Gene* 108:201–210; Benton et al., *Molecular and Cellular Biology* (1990) *Molecular and Cellular Biology* 10:353–360; Elroy-Stein and Moss (1990) Proceedings, *Proc. Natl. Acad. Sci.: USA* 87:6743–6747; Moss et al., (1990) *Nature* 348:91–92; Elroy-Stein et al., (1989) Proceedings, *Proc. Natl. Acad. Sci.:USA* 86:6126–6130; and Rosenberg et al., (1987) *Gene* 56:125–135, herein incorporated by reference.

Regulator polypeptides or transactivators also include DNA binding proteins which are necessary for transcription activation of specific promoters. Binding domains of one protein may be fused to activity domains of another protein to form chimeras of such DNA binding proteins, such as GAL4/VP16 (Carey et al. (1989), *J. Mol. Biol.*, 209:423-432; Cress et al. (1991) *Science*, 251:87-90; and Sadowski et al. (1988), *Nature*, 335:563-564). Likewise, the binding domain of other proteins, i.e., Lex A (Brent and Ptashne, (1985), *Cell*, 43:729-736, which describes a Lex A/GAL4 transcriptional activator) can be utilized.

Translational activators are exemplified by the cauliflower mosaic virus translational activator (TAV). See, for example Futterer and Hohn (1991) *EMBO J.* 10:3887-3896. In this system a dicistronic mRNA is produced. That is, two coding regions are transcribed in the same mRNA from the same promoter. In the absence of TAV, only the first cistron is translated by the ribosomes. However, in cells expressing TAV, both cistrons are translated. The coding region for a polypeptide capable of disrupting the formation of viable pollen is placed in the position of the second cistron.

The expression cassette, expression cassette 1, utilized to transform parent 1 comprises an anther 5' regulatory region operably linked to the first polypeptide, the transactivator. The 5' regulatory regions of the invention include nucleotide sequences necessary for expression, i.e. the promoter region. The construct may also include any other necessary regulators such as terminators, (Guerineau et al., (1991), *Mol. Gen. Genet.*, 226:141-144; Proudfoot, (1991), *Cell*, 64:671-674; Sanfacon et al., (1991), *Genes Dev.*, 5:141-149; Mogen et al., (1990), *Plant Cell*, 2:1261-1272; Munroe et al., (1990), *Gene*, 91:151-158; Ballas et al., (1989), *Nucleic Acids Res.*, 17:7891-7903; Joshi et al., (1987), *Nucleic Acid Res.*, 15:9627-9639); nuclear localization signals (Kalderon et al., (1984) *Cell*, 39:499-509; and Lassner et al., (1991) *Plant Molecular Biology*, 17:229-234); plant translational consensus sequences (Joshi, C. P., (1987), *Nucleic Acids Research*, 15:6643-6653), introns (Luehrsen and Walbot, (1991), *Mol. Gen. Genet.*, 225:81-93) and the like, operably linked to the nucleotide sequence of the transactivator.

The expression cassette, expression cassette 2, utilized to transform parent 2 comprises a nucleotide sequence upon which the transactivator acts operably linked to a coding region of interest. Additional regulating nucleotide regions may also be included, such as terminators, promoters, leader sequences and the like. Such regions are operably linked to the coding region.

It may be beneficial to include 5' leader sequences in the expression cassette 2 construct. Such leader sequences can act to enhance translation. Translational leaders are known in the art and include:

Picornavirus leaders, for example, EMCV leader (Encephalomyocarditis 5' noncoding region) (Elroy-Stein, O., Fuerst, T. R., and Moss, B. (1989) *PNAS USA* 86:6126-6130);

Potyvirus leaders, for example, TEV leader (Tobacco Etch Virus) (Allison et al., (1986); MDMV leader (Maize Dwarf Mosaic Virus); *Virology*, 154:9-20), and Human immunoglobulin heavy-chain binding protein (BiP), (Macejak, D. G., and Sarnow, P., (1991), *Nature*, 353:90-94;

untranslated leader from the coat protein mRNA of alfalfa mosaic virus (AMV RNA 4), (Jobling, S. A., and Gehrke, L., (1987), *Nature*, 325:622-625;

Tobacco mosaic virus leader (TMV), (Gallie, D. R. et al., (1989), *Molecular Biology of RNA*, pages 237-256; and Maize Chlorotic Mottle Virus leader (MCMV) (Lommel, S. A. et al., (1991), *Virology*, 81:382-385. See also, Della-Cioppa et al., (1987), *Plant Physiology*, 84:965-968.

Either a plant terminator, a T7 terminator or both may be utilized in expression cassette 2. See, Rosenberg et al., (1987), *Gene*, 56:125; Guerineau et al., (1991), *Mol. Gen. Genet.*, 226:141-144; Proudfoot, (1991), *Cell*, 64:671-674; Sanfacon et al., (1991), *Genes Dev.*, 5:141-149; Mogen et al., (1990), *Plant Cell*, 2:1261-1272; Munroe et al., (1990), *Gene*, 91:151-158; Ballas et al., (1989), *Nucleic Acids Res.*, 17:7891-7903; Joshi et al., (1987), *Nucleic Acid Res.*, 15:9627-9639).

Particular expression cassettes will be discussed in more detail for different transactivator systems and exemplified in the experimental section.

In one embodiment of the invention, a T7 polymerase system is utilized. The T7 bacteriophage harbours a gene coding for an RNA polymerase which recognizes a phage specific promoter. The polymerase and the phage promoters have unique properties which prevent interference with expression of host genes.

The T7 RNA polymerase is a monomeric enzyme of 100 kD whereas most other polymerases are more complex. The T7 promoter consists of 23 bp which are not encountered in other prokaryotic or eukaryotic promoters. See, Dunn et al., (1983) *J. Mol. Biol.* 166:477-535; Davanloo et al., (1984) Proceedings *Proc. Natl. Acad. Sci. USA* 81:2035-2079; and Moffatt et al., (1984) *J. Mol. Biol.* 173:265-269.

To use a T7 polymerase system to produce male-sterile plants, parent 1 is transformed with an expression cassette comprising an anther 5' regulatory region operably linked to a nucleotide sequence encoding the T7 polymerase. A nuclear location signal (NLS) such as the SV40 nuclear location signal may also be incorporated into the construct. See, for example, Kalderon et al., (1984) *Cell* 39:499-509; Dunn et al., (1988) *Gene* 68:259-266; Hunt T. (1989) *Cell* 59:949-951; and Lassner et al., (1991) *Plant Molecular Biology* 17:229-234, which disclosures are herein incorporated by reference. A plant translational consensus sequence (Joshi, C. P. (1987) *Nucleic Acids Research* 15:6643-6653) may be also included, as well as plant termination signals and introns.

Anther-specific promoters are known in the art. By utilizing anther-specific promoters, the resulting transgenic plants will express the T7 polymerase only in the anther of the plant. Anther-specific promoters are set forth in U.S. application Ser. No. 908,242 filed Jul. 2, 1992, which disclosure is herein incorporated by reference.

In the case of promoter DNA sequences, "anther-specific" describes regulatory sequences which direct the transcription of associated coding sequences so that the corresponding messenger RNA is present in anther tissue in concentrations at least about 100-fold that observed in other tissues.

The expression cassette utilized to transform parent 2 comprises a T7 promoter operably linked to a nucleotide sequence which encodes RNA or a polypeptide which disrupts formation of viable pollen when expressed. Such polypeptides include but are not limited to:

Diphtheria Toxin A-chain (DTA), which inhibits protein synthesis, Greenfield et al., (1983), *Proc. Natl. Acad., Sci.:USA*, 80:6853; Palmiter et al., (1987), *Cell*, 50:435;

Pectate lyase pelE from Erwinia chrysanthemi EC16, which degrades pectin, causing cell lysis. Keen et al., (1986), *J. Bacteriology*, 168:595;

T-urf13 (TURF-13) from cms-T maize mitochondrial genomes; this gene encodes a polypeptide designated URF13 which disrupts mitochondrial or plasma membranes. Braun et al., (1990), *Plant Cell*, 2:153; Dewey et al., (1987), *Proc. Natl. Acad. Sci.:USA*, 84:5374; Dewey et al., (1986), *Cell*, 44:439;

Gin recombinase from phage Mu a gene, which encodes a site-specific DNA recombinase which will cause genome rearrangements and loss of cell viability when expressed in cells of plants. Maeser et al., (1991), *Mol. Gen. Genet.*, 230:170–176;

Indole acetic acid-lysine synthetase (iaaL) from *Pseudomonas syringae*, which encodes an enzyme that conjugates lysine to indoleacetic acid (IAA). When expressed in the cells of plants, it causes altered developments due to the removal of IAA from the cell via conjugation. Romano et al., (1991), *Genes and Development*, 5:438–446; Spena et al., *Mol. Gen. Genet.*, (1991), 227:205–212; Roberto et al., *Proc. Natl. Acad. Sci.:USA*, 87:5795–5801; and, CytA toxin gene from *Bacillus thuringiensis Israeliensis* which encodes a protein that is mosquitocidal and hemolytic. When expressed in plant cells, it causes death of the cell due to disruption of the cell membrane. McLean et al., (1987), *J. Bacteriology*, 169:1017–1023; Ellar et al., (1990), U.S. Pat. No. 4,918,006.

Such polypeptides also include Adenine Phosphoribosyltransferase (APRT) (Moffatt and Somerville, (1988), *Plant Physiol.*, 86:1150–1154); DNAse, RNAse; protease; salicylate hydroxylase; etc.

It is further recognized that the T7 promoter could be operably linked to RNA which is capable of disrupting the formation of viable pollen. The RNA of the invention includes antisense RNA as well as ribozymes. Antisense RNA can be utilized which will hybridize with mRNA from a gene which is critical to pollen formation or function, i.e. APRT. In this manner, the antisense RNA will prevent expression of the necessary genes resulting in no pollen formation.

Alternately, ribozymes can be utilized which target mRNA from a gene which is critical to pollen formation or function. Such ribozymes will comprise a hybridizing region of at least about nine nucleotides which is complementary in nucleotide sequence to at least part of the target RNA and a catalytic region which is adapted to cleave the target RNA. Ribozymes are described in EPA No. 0 321 201 and WO88/04300 herein incorporated by reference. See, also Haseloff and Gerlach, (1988), *Nature*, 334:585–591; Fedor and Uhlenbeck, (1990), *Proc. Natl. Acad. Sci.:USA*, 87:1668–1672; Cech and Bass, (1986), *Ann. Rev. Biochem.*, 55:599–629; Cech, T. R., (1987), 236:1532–1539; Cech, T. R. (1988) *Gene*, 73:259–271; and, Zang and Cech, (1986), *Science*, 231:470–475.

When parent 1 is crossed with parent 2, the progeny contain both expression cassettes. Therefore, the T7 polymerase drives expression of the coding sequence under the control of the T7 promoter. A polypeptide or RNA is expressed which disrupts the formation of viable pollen resulting in male-sterility.

Having described the T7 polymerase system in detail, one of skill in the art will recognize that other transactivators may be utilized to obtain the same effect.

Other known transactivators include, but are not limited to GAL4 (Carey et al., (1989), *J. Mol. Biol.*, 209:423–432; Ginger et al., (1985), *Cell*, 40:767–774); VP16 (Cress and Triezenberg (1991), *Science*, 251:87–90); GAL4-VP16 (Sadowski et al., (1988), *Nature*, 335:563–564); etc. See also, Ma and Ptashne, (1987), *Cell*, 43:729–736; Hope and Struhl, (1986), *Cell*, 46:885–894; and Gill and Ptashne, (1987), *Cell*, 51:121–126. Such transactivators activate transcription in yeast, plant, insect and mammalian cells. These proteins typically contain two parts. One part directs DNA binding and the other, the activating region, presumably interacts with some component of the transcriptional machinery. Thus, fusions such as GAL4-VP16; GAL4-c1 may be utilized.

The transactivators GAL4/VP16 and GAL4/c1 can be utilized to transactivate a promoter with at least one GAL4 binding site. In this system, parent 1 is transformed with an expression cassette comprising an anther 5' regulatory region operably linked to GAL4/VP16 or GAL4/c1. Parent 2 is transformed with an expression cassette comprising in 5' to 3' orientation, a GAL4 binding site, a minimal promoter or 5' regulatory region and the coding region of interest. By minimal promoter is intended that the basal promoter elements are inactive or nearly so without upstream activation.

The offspring from a cross of parent 1 and parent 2 will be male-sterile as the GAL4 transactivator will direct expression of the polypeptide or anti-sense RNA which will disrupt formation of viable pollen.

As discussed earlier, translational activators can also be utilized. In this system, Parent 1 is transformed with an expression cassette comprising an anther 5' regulatory region operably linked to the cauliflower mosiac virus translation activator (TAV). Parent 2 is transformed with an expression cassette comprising an anther specific promoter operably linked to a dicistronic mRNA wherein the second cistron encodes a cell toxin. Crossing parents 1 and 2 results in male sterile offspring as both cistrons of the dicistronic mRNA will be translated in the presence of TAV. See, Bonneville et al., (1987), *Cell*, 59:1135–1143; Futterer and Hohn, (1991), *EMBO J.*, 10:3887–3896; Gowda et al., (1988), *Proc. Natl. Acad, Sci., USA*, 86:9203–9207; Scholthof et al., (1992), *J. Virology*, 66:3131–3139; and EP 298 918 filed Jul. 10, 1987.

In some instances it may be useful to combine the use of more than one transactivator in a single system. For example, transcriptional activation via T7 polymerase or GAL4/VP16 can be combined with translational activation. This combination may provide a tighter control of unwanted expression of the toxin gene in the absence of the transactivator.

Methodologies for the construction of plant expression cassettes as well as the introduction of foreign DNA in to plants is generally described in the art. Generally, for the introduction of foreign DNA into plants Ti plasmid vectors have been utilized for the delivery of foreign DNA as well as direct DNA uptake, liposomes, electroporation, micro-injection, and the use of microprojectiles. Such methods had been published in the art. See, for example, Guerche et al., (1987) *Plant Science* 52:111–116; Neuhause et al., (1987) *Theor. Appl. Genet.* 75:30–36; Klein et al., (1987) *Nature* 327:70–73; Howell et al., (1980) *Science* 208:1265; Horsch et al., (1985) *Science* 227:1229–1231; DeBlock et al., (1989) *Plant Physiology* 91:694–701; *Methods for Plant Molecular Biology* (Weissbach and Weissbach, eds.) Academic Press, Inc. (1988); and *Methods in Plant Molecular Biology* (Schuler and Zielinski, eds.) Academic Press, Inc. (1989). It is understood that the method of transformation will depend upon the plant cell to be transformed.

It is further recognized that the components of the expression cassette may be modified to increase expression. For example, truncated sequences, nucleotide substitutions or other modifications may be employed.

It may also be beneficial to remove nucleotides in the T7 promoter sequence to prevent potential stem-loop structures in the RNA. Such nucleotides can be removed, for example, using PCR technology as set forth below in the Experimental Section. Likewise, a poly A chain may be included in the expression cassette adjacent to the terminator. For example, in expression cassette 2, about 25 to about 90 A nucleotides may be inserted 5′ to the T7 terminator.

Other methods such as transplicing may also be employed utilizing the splice donor and splice acceptor sites of known genes such as the Adh1 gene of maize. See. Dennis et al., (1984), *Nucleic Acids Research*, 12:3983–4000. Such a system involves three expression cassettes. The following are typical cassettes which could be utilized in a T7 system. Cassette 1 comprises an anther-specific promoter operably linked to a nucleotide sequence encoding a transactivator, e.g. T7 polymerase.

Cassette 2 comprises the target nucleotide sequence, T7 promoter, operably linked to a nucleotide sequence comprising a splice acceptor site. The acceptor site is operably linked to a nucleotide sequence comprising the 3′ portion of the coding region of a polypeptide or RNA capable of disrupting the formation of viable pollen.

Cassette 3 comprises a nucleotide sequence encoding a promoter capable of directing expression in anther tissue, operably linked to a nucleotide sequence comprising the 5′ coding region of the polypeptide or RNA capable of disrupting the formation of viable pollen which is operably linked to a splice donor site. As discussed earlier, the cassettes may also comprise leader sequences, terminators, etc. Parent plant 1 can be stably transformed with cassette 1, or alternatively, cassettes 1 and 3 while Parent plant 2 will contain cassettes 2 and 3, or alternatively cassette 2, respectively. In either situation crossing Parent 1 and Parent 2 results in male-sterile progeny.

Transformed plants are regenerated. The presence of the stably integrated expression cassette into the transformed parent plants may be ascertained by southern hybridization techniques or PCR analysis, known in the art. Expression of the transactivator may be determined by utilizing northern blot techniques.

Therefore, the present system can be utilized in any plant which can be transformed and regenerated. The method eliminates the necessity of manipulating floral structures and avoids the necessity of hand emasculation and fertilization.

The parent plants containing the respective stably integrated expression cassettes are both male fertile and can be made homozygous and maintained indefinitely. To obtain male-sterile seed, homozygous lines of parent 1 and 2 are crossed using a technique such as detasseling of one line and using the other as a pollinator, such that no self seed is produced. The male-sterile offspring can then be utilized as female parents in any cross to produce hybrid seed. About 75% of the resulting hybrid seeds will give rise to male fertile plants. Thus, for the purpose of producing hybrid seed, standard crossing of different lines with the male-sterile plants and subsequent analysis of the progeny to select a line with superior agronomic traits are performed. See, generally, International Patent Application Number WO 90/08828.

While the T7 polymerase system is useful in the above-described dual system for the production of male-sterile plants, it is also recognized that a T7 expression system can be utilized for high level expression of nucleotide sequences in plants. The system also provides tissue-specific expression or other selective expression of coding sequences in a plant.

In this manner, a single plant can be transformed with two expression cassettes. A first expression cassette comprises a T7 polymerase operably linked to a promoter capable of directing expression in a plant cell. Any promoter capable of directing expression can be utilized and can be chosen for specific expression; e.g. tissue-specific promoter, developmental stage-specific promoter, inducible promoter, etc. Specific promoters, for example, include chemical inducible promoters (U.S. patent application Ser. No. 678,378) and seed specific promoters (Ellis et al., (1988), *Plant Mol. Biol.*, 10:203–214). As described earlier, the first expression cassette may additionally comprise nuclear location signals, terminator sequences, plant translational consensus sequences, etc.

The second expression cassette comprises a coding sequence operably linked to a nucleotide sequence encoding T7 promoter. The second expression cassette may also comprise 5′ leader sequences, terminator sequences, etc.

When both expression cassettes have been stably integrated into a single plant, the T7 polymerase will drive expression of the coding sequence operably linked to the T7 promoter.

It is recognized that the two expression cassettes may be part of a single vector or nucleic acid sequence or may be housed on separate vectors. Likewise, while a single plant in most instances will be transformed with each cassette, it may be beneficial at times to transform one plant, parent 1, with expression cassette 1 and another plant, parent 2, with expression cassette 2 and obtain progeny with both expression cassettes by crossing parents 1 and 2.

Because transcription by T7 RNA polymerase is highly active, this system may be utilized to increase the production of specific gene products which are produced in low quantities in plants. The method is also useful for increasing tissue or other specific gene products. Generally, at least about a two fold to greater than a 100 fold, more specifically about 4 fold to about 50 fold, increase in expression can be seen using a T7 system.

The T7 RNA polymerase is very selective for specific promoters that are rarely encountered in DNA unrelated to T7 DNA. Efficient termination signals are also rare. Therefore, the T7 RNA polymerase expression system can make complete transcripts of almost any DNA that is placed under control of a T7 promoter. Accordingly, the T7 expression system can be used to express a wide variety of products such as seed storage proteins with preferred amino acid composition; pharmaceutical proteins; proteins involved in starch, lipid or protein synthesis; insecticidal or disease resistance proteins; proteins which increase the nutritional quality of plants or seeds; antifungal, antibacterial or antiviral proteins; proteins that lead to the production of other proteins that render the plant resistant to insects or diseases; assembly proteins or proteins that are required for the production of other proteins; and the like.

As discussed earlier, methods for manipulation of nucleic acid sequences and for transformation and regeneration of plants are known in the art.

Having generally described the invention, the following examples are offered by way of illustration and not by way of limitation.

EXPERIMENTAL

Example 1

Addition of a plant translational consensus sequence to the T7 RNA polymerase gene The translational start site of the T7 RNA polymerase gene (with the SV40 NLS) of pAR3283 (Dunn et al., Gene 68:259-255 (1988) was modified to include a plant translational consensus sequence (Joshi, C. P., NAR 15, 6643-6653 (1987)). The BglII to NruI fragment of pAR3283 was replaced with a BglII-NruI PCR generated fragment in which the sequence TAAA-CAATG, following the BglII site, replaced the sequence before the T7 translational start site. The nucleotides after the translational start site were not modified to conform to the plant consensus sequence (TAAA-CAATGGCT) because an asparagine to alanine substitution would result.

Example 2

Fusion of the 35S CaMV promoter to the T7 RNA polymerase gene

The T7 RNA polymerase gene containing the SV40 nuclear localization signal (NLS) and a plant translational consensus sequence was excised as a BglII-BamHI fragment and cloned into the BamHI site of pCIB710 (Rothstein et al., Gene 53:153-161 (1987)). The resulting plasmid, pJS175, contains the 35S CaMV promoter, T7 RNA polymerase gene (SV40 NLS, plant translational consensus sequence) and the 35S CaMV poly A addition site.

Example 3

T7 promoter/terminator constructions and fusions to the GUS gene

The T7 promoter and T7 terminator from pET-3 (Rosenberg et al., Gene 56, 125 (1987)) was inserted as a BglII fragment into BamHI-cleaved pUC19 to make pAT26 and into BamHI-cleaved bluescript SK to make pAT10. The 3′ Sac I site of the GUS gene from pBI121 (Clontech) was adapted to contain to a Bam HI site and cloned into the Bam HI site between the T7 promoter and terminator of pAT10 to make pAT11.

In pAT27, the nucleotides +9 to +26 of the T7 promoter were removed by PCR from pAT26 in order to eliminate a potential stem-loop structure in the RNA. A 35S CaMV poly A addition signal was inserted into the BamHI site of pAT27 by adding a BglII site by PCR on the 3′ end of the fragment, resulting in pAT28. The GUS gene from pAT11 was inserted into the BamHI site of pAT28 to make pAT30 and into the BamHI site of pAT27 to make pAT32. pJS261 was constructed by replacing the T7 terminator of pAT26 with a BamHI-EcoRI fragment containing the 35S terminator, T7 terminator from pAT28. A BamHI fragment containing the TEV leader-GUS gene from pAT31 was then inserted in the BamHI site.

Example 4

Translational constructs using the tobacco etch virus leader

The tobacco etch virus 5′ nontranslated leader (nucleotides +6 to +143 of the genomic RNA, Allison et al., Virology 154:9-20 (1986)), with a BamHI site on the 5′ end and a NcoI site on the 3′ end, was translationally fused to a GUS gene (NcoI-SacI fragment) into bluescript SK to make pAT29. The SacI site of pAT29 was adapted to contain to BamHI and the BamHI fragment containing the TEV leader-GUS gene was inserted into the BamHI site of pAT28 to make pAT31.

Example 5

Protoplast transformation and GUS fluorometric assays

Nicotiana tabacum protoplasts were transformed as described in Negrutiu, I. et al., PMB 8:363-373 (1987) and GUS fluorometric assays were performed as in Jefferson, R. A., PMB Reporter 5:387-405 (1987).

Methods for production of maize protoplasts are described in U.S. patent application Ser. No. 772,027 filed Oct. 4, 1991, herein incorporated by reference.

Example 6

Transcription from the T7 promoter in transient experiments

Maize protoplasts were cotransformed with the 35S promoter driving T7 RNA polymerase (pJS175) and the T7 promoter/GUS gene/T7 terminator (pAT11). As a negative control, protoplasts were also cotransformed with a 35S promoter/luciferase gene (pCIB1700) and with pAT11. Protoplasts transformed with 35S/GUS (pCIB246) were a positive GUS control. RNA was isolated from protoplasts according to the guanidinium thiocyantate-phenol-chloroform method described by Goodall et al., Methods in Enzymology 181:148-161 (1990). Duplicate northerns were probed with a T7 RNA polymerase and a GUS probe. Only RNA from the protoplasts transformed with pJS175 and pAT11 hybridized to the T7 RNA polymerase probe. RNA from protoplasts transformed with pJS175 alone and with pJS175/pAT11 hybridized to the GUS probe, showing that T7 RNA polymerase is transcribing off the T7 promoter in plant cells. GUS RNA levels transcribed from the T7 promoter were 10-fold higher than the pCIB246 control.

Example 7

GUS expression using the Tobacco Etch Virus leader for translation of T7 transcripts Tobacco protoplasts were cotransformed with the 35S CaMV promoter driving T7 RNA polymerase (pJS175) and T7 promoter—GUS fusions with and without the TEV leader (pAT31, pJS261). GUS fluormotetric assays were done (Table I). GUS enzyme activity (4-fold higher than the 35S/GUS control) was seen in T7 constructs only when the TEV leader was present.

TABLE I

Transient expression experiment using the TEV leader pCIB 246  35S/GUS
pJS 175   35S/T7 RNA polymerase
pJS 179   35S/luciferase TABLE I-continued

| | | |
|---|---|---|
| pAT11 | T7 promoter/GUS/T7 terminator | |
| pJS261 | T7 promoter/TEV leader/GUS/35S terminator/T7 terminator | |
| pAT31 | T7 promoter (stem loop removed)/TEV leader/GUS/35S terminator/T7 terminator | |

| | Specific GUS Activity (nm MU/μg protein/min.) | Fold increase over pCIB246 |
|---|---|---|
| pCIB 246 | 20.5 ± 4 | |
| pJS 179/pAT11 | 0.021 ± 0.007 | |
| pJS 175/pAT11 | 0.013 ± 0.004 | |
| pJS 175/pJS261 | 14.17 ± 0.45 | 0.7 |
| pJS 175/pAT31 | 80.8 ± 5 | 3.9 |

Example 8

Fusion of an anther-specific promoter to the T7 RNA polymerase gene

The T7 RNA polymerase gene containing the SV40 nuclear localization signal and a plant translational consensus sequence was excised as a Bgl II-Bam HI fragment and cloned into the Bam HI site of pLC250. In pLC250, a tapetal-specific tobacco anther promoter, ant32, was cloned into the Sal I, Xba I sites of the Agrobacterium binary plasmid vector pBI101 (Clontech, Palo Alto, Calif.). The GUS gene had previously removed from pBI101 with Sma I, Sac I and the Sac I site had been blunted. The resulting plasmid, pAT20, contains the ant32 tobacco anther promoter, the T7 RNA polymerase gene (SV40 NLS, plant translational consensus sequence) and a nos terminator.

Example 9

Construction of plant transformation vectors containing an anther-specific promoter driving T7 RNA polymerase and the T7 promoter driving the Diphtheria toxin gene A plant transformation vector was constructed containing an anther-specific promoter driving T7 RNA polymerase and a T7 promoter driving the Diphtheria toxin A-chain (DTA) coding sequence (Palmiter et al, Cell 50:435-443). A T7 promoter/TEV leader/DTA coding sequence/35S terminator/T7 terminator cassette was made by excising the GUS gene from pAT30 with Bam HI and inserting in a TEV leader Bam HI-Nco I fragment from pAT29 and a DTA coding sequence Nco I-Bgl II fragment, resulting in pTG28. pTG32 is a vector for plant transformation containing both components and was made by adaptoring the 3' Eco RI site of pTG28 to Hind III and inserting the Hind III fragment into pAT20.

The anther-specific promoter driving T7 RNA polymerase and the T7 promoter driving DTA can also be independently transformed into plants and then crossed in order to produce male-sterile plants. pTG35 contains only the T7 promoter driving DTA in a plant transformation vector and was constructed by adapting the 3' Eco RI site of pAT28 to Sal I and cloning into the Sal I site of the plant transformation vector pCIB905. Plants transformed with pTG35 can be crossed to pAT20 transformants.

Example 10

Production of transgenic plants

Tobacco leaf discs were transformed with pTG32, pAT20 and pTG35 as described in Horsch et al., Science 227:1229-1231 (1985) and the presence of transforming DNA was confirmed using PCR.

Example 11

Analysis of plants transformed with an anther-specific promoter driving T7 RNA polymerase and the T7 promoter driving DTA The flower morphology of 13 plants transformed with pTG32 was observed. 11 plants were male-sterile and 9 of the 11 plants were shown to be female-fertile by backcrossing with wild-type tobacco.

Example 12

Plant transformation vectors for GUS expression from the T7 promoter

The 35S CaMV promoter driving the T7 RNA polymerase and the T7 promoter driving the GUS gene were cloned into a plant transformation vector. As a control, the 35S CaMV promoter driving luciferase and the T7 promoter driving the GUS gene were also cloned. The T7 promoter (stem loop removed) /TEV leader/GUS gene/35S terminator/T7 terminator were removed from pAT31 with Xba I, Eco RI and cloned into the plant transformation vector pCIB200 in pAT34. The 5' Sac I site of the 35S promoter/T7 RNA polymerase/nos terminator fragment was adapted to contain to Xba I (Sac I site destroyed) and cloned into the Xba I site pAT34 to make pAT35. For the control, a luciferase gene was cloned into the BamHI site of pCIB770 (Rothstein et al., Gene 53:153-161 (1987)) in pAT36. In pAT37, the EcoRI site of pAT31 was adapted to contain Sal I (Eco RI destroyed) and the Sal I fragment containing the T7 promoter/TEV leader/GUS gene/35S terminator/T7 terminator was cloned into the Sal I site of pAT36. In both pAT35 and pAT37, clones were chosen which have transcription of the two genes in opposite orientations away from each other.

Example 13

Anti-sense inhibition using T7 polymerase and T7 promoters

In pCIB3217, the T7 promoter was inserted in an anti-sense direction after a 35S promoter/GUS/35S terminator cassette in puc 19. This cassette is cloned into a plant transformation vector and is crossed to a plant transformed with 35S promoter/T7 RNA polymerase (pCIB3210). GUS enzyme activity of progeny carrying both T7 polymerase and the GUS gene/anti-sense T7 promoter is compared to progeny carrying only the GUS gene/anti-sense T7 promoter.

Example 14

Construction of vectors containing the GAL4 binding site/minimal 35S CAMVpromoter fused to GUS and Diphtheria toxin The GAL4 consensus binding site (Giniger et al., Cell 40:767-774 (1985) was fused to the CAMV 35S minimal promoter (−46 to +1, Benfey et al., EMBO 9:1677-1684 (1990)) by incorporating the binding site into a PCR primer. The PCR generated band containing the binding site and the minimal promoter contained HindIII, XbaI ends and was cloned into pBI101. pLP3 contains the GAL4 binding site/minimal 35S promoter/GUS gene/nos termininator in a plant transformation vector. This cassette was excised from pLP3 with HindIII, EcoRI and cloned into bluescript to make pLP4.

The GAL4 binding site/minimal 35S promoter was fused to the DTA coding sequence. The GUS gene was first removed from pBI101 by excising with SmaI and SacI, blunting the SacI site, and religating the plasmid back together. The GAL4 binding site/minimal 35S promoter was cloned into the HindIII, XbaI sites and the DTA gene was cloned as a BglII fragment into the BamHI site of the vector. pLP1 contains the GAL4 binding site/35S minimal promoter/DTA coding sequence/nos terminator in a plant transformation vector.

Example 15

GUS expression using the GAL4/VP16 transactivator

Maize protoplasts were cotransformed with a 35S promoter/GAL4/VP16 gene (pGAL4/VP1-Goff et al., (1991). *Genes and Development,* 5:298–309) and a GAL4 binding site/minimal 35S promoter/GUS gene (pLP4). GUS fluorometric assays were performed (Table II). GUS enzyme activity was 20 fold higher from the GAL4 binding site/minimal 35S promoter when the GAL4/VP16 transactivator was present.

TABLE II

Transient expression experiment using GAL4/VP16 transactivation

| pLP4 | GAL4 binding site/minimal 35S promoter/GUS |
| pGAL4/VP1 | 35S promoter/Adh1 intron/GAL4/VP16 |

| | Specific GUS Activity (nm MU/µg protein) | Fold increase over pLP4 |
|---|---|---|
| no DNA | 0.02 ± 0.0 | |
| pLP4 | 0.26 ± 0.15 | |
| pLP4/ pGAL4/VP1 | 5.25 ± 1.20 | 20 |

Example 16

Fusion of an anther promoter to GAL4/VP16

The GAL4/VP16 fusion was excised as a BamHI fragment from pGAL4/VP1 and inserted into the BamHI site of pLC250. The resulting plasmid, pLP2, contains an anther-specific promoter/GAL4/VP16 / nos terminator in a plant transformation vector. Transformants containing pLP2 can be crossed to plants transformed with pLP3 in order to get activation of the GUS gene or to plants transformed with pLP1 in order to produce male-sterile plants.

Although the foregoing invention has been described in some detail by way of illustration and example for purposes of clarity of understanding, it will be obvious that certain changes and modifications may be practiced within the scope of the appended claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

What is claimed is:

1. A method for producing male-sterile plants, said method comprising:

transforming a first parent plant cell with a first expression cassette, said cassette comprising a nucleotide sequence encoding an anther-specific 5' regulatory region operably linked to a nucleotide sequence which encodes a transactivator polypeptide not naturally associated with plants, wherein said transactivator polypeptide turns on transcription that is otherwise off in the absence of said transactivator polypeptide;

regenerating a transformed plant, Parent 1, from said first transformed plant cell;

transforming a second parent plant cell with a second expression cassette comprising a target nucleotide sequence which is activated by said transactivator polypeptide, operably linked to a leader sequence, said leader sequence operably linked to a nucleotide sequence which encodes anti-sense RNA which disrupts the formation of viable pollen or a polypeptide which disrupts the formation of viable pollen;

regenerating a transformed plant, Parent 2, from said second transformed plant cell; and crossing said Parent 1 with Parent 2 to obtain male-sterile offspring.

2. The method of claim 1, wherein said transactivator polypeptide is a T7 polymerase.

3. The method of claim 2, wherein said target nucleotide sequence is a T7 5' regulatory region.

4. The method of claim 2, wherein said T7 polymerase further comprises a nuclear localization signal sequence.

5. The method of claim 1, wherein said transactivator polypeptide is a DNA binding protein.

6. The method of claim 5, wherein said DNA binding protein is GAL4 protein.

7. The method of claim 1, wherein said anti-sense RNA hybridizes to a message from a coding sequence that is critical to pollen formation or function.

8. The method of claim 1, wherein said polypeptide which disrupts the formation of viable pollen is selected from diptheria toxin A, pectate lyase, T-urf13, gin recombinase, indole acetic acid-lysine synthetase, cytA toxin, alenine phosphorbosyltransferase, RNAse, DNAse or protease.

9. The method of claim 8, wherein said polypeptide which disrupts the formation of viable pollen is diphtheria toxin A.

10. The method of claim 6, wherein said expression cassette of Parent 2 further comprises a GAL4 binding site linked to a minimal 35S promoter operably linked to said nucleotide sequence which encodes anti-sense RNA which disrupts the formation of viable pollen or a polypeptide which disrupts the formation of viable pollen.

11. The method of claim 2, wherein said expression cassette of parent 2 further comprises a T7 terminator sequence.

12. The method of claim 2, wherein said expression cassette of parent 2 further comprises a plant terminator sequence., 13. The method of claim 11, wherein said expression cassette of parent 2 further comprises a second terminator sequence which is a plant terminator sequence.

14. A method for producing hybrid seed from plants, said method comprising:

(a) producing male-sterile plants by:

(i) transforming a first parent plant cell with a first expression cassette which comprises a nucleotide sequence encoding an anther-specific 5' regulatory region which is operably linked to a nucleotide sequence encoding a transactivator polypeptide not naturally associated with plants, wherein said transactivator polypeptide turns on transcription that is otherwise off in the absence of said transactivator polypeptide;

(ii) regenerating a transformed plant, Parent 1, from said first transformed plant cell;

(iii) transforming a second parent plant cell with an expression cassette which comprises a target nucleotide sequence which is activated by said transactivator operably linked to a leader sequence, said leader sequence operably linked to a nucleotide sequence which encodes anti-sense RNA which disrupts the formation of viable pollen or a polypeptide which disrupts the formation of viable pollen;

(iv) regenerating a transformed plant, Parent 2, from said second transformed plant cell; and (v) crossing said Parent 1 with said Parent 2 to produce male-sterile offspring; and (b) crossing said male-sterile offspring with a selected fertile line to obtain hybrid seed.

15. A male-sterile plant which comprises a stably integrated first expression cassette comprising a nucleotide sequence encoding an anther-specific promotor which is operably linked to a nucleotide sequence encoding a transactivator polypeptide not naturally associated with plants, wherein said transactivator polypeptide turns on transcription that is otherwise off in the absence of said transactivator polypeptide; and a second expression cassette comprising a target nucleotide sequence, which is activated by said transactivator polypeptide, operably linked to a leader sequence, said leader sequence operably linked to a nucleotide sequence which encodes anti-sense RNA which disrupts the formation of viable pollen or a polypeptide which disrupts the formation of viable pollen.

16. A male-sterile plant produced by the method of claim 1.

* * * * *